United States Patent [19]

Burgio

[11] Patent Number: 5,333,619

[45] Date of Patent: Aug. 2, 1994

[54] METHOD FOR RIGID TISSUE BIOPSY

[76] Inventor: Vito L. Burgio, Via Nomentana, 44, Rome, Italy

[21] Appl. No.: 103,982

[22] Filed: Aug. 9, 1993

[51] Int. Cl.$^5$ ............................................. A61B 10/00
[52] U.S. Cl. ................................................... 128/754
[58] Field of Search ....................... 128/749, 751–753, 128/754; 696/167, 170

[56] References Cited

U.S. PATENT DOCUMENTS 4,785,826  11/1988  Ward .................................. 128/754
5,111,828  5/1992  Kornberg et al. .................. 128/754

FOREIGN PATENT DOCUMENTS 567447  9/1977  U.S.S.R. .............................. 128/754
1537232  1/1990  U.S.S.R. .............................. 128/754

OTHER PUBLICATIONS

"New Biopsy Instruments", Aksenova et al., Biomed. Engin. Mar. 1980.

*Primary Examiner*—Max Hindenburg
*Attorney, Agent, or Firm*—Harison & Egbert

[57] ABSTRACT

The present invention relates to a method for obtaining a biopsy from rigid tissue using a needle with a tapered end and a plate insertable into the needle to fit between the needle and tissue within the needle. The needle is then rotated to obtain a biopsy specimen.

11 Claims, 1 Drawing Sheet

METHOD FOR RIGID TISSUE BIOPSY

TECHNICAL FIELD

The present invention relates to apparatus used in conjunction with hypodermic needles. More particularly, the present invention relates to devices used for carrying out a biopsy.

BACKGROUND ART

Needles conventionally used for percutaneous biopsies of hard tissue, particularly osteomedullary tissue, consist of a cylinder of varying length and diameter with a proximal end furnished with a handle and a distal end that is more tapered than the rest of the needle and ends in a hole with a sharp edge. Through the simultaneous pushing on and rotation of the needle on its axis in the tissue being biopsied, this end cuts out a cylinder that the needle takes into its cavity. Afterward, in order to extract this biopsy cylinder from the tissue it is necessary to interrupt the continuity of the distal end with the rest of the tissue penetrated by the needle. To accomplish this with conventional methods, the needle's handle is oscillated on a plane perpendicular to the needle's axis, with a pin at the point of entry of the tissue. This maneuver results in a break in the connections between the distal end of the biopsy and the remaining tissue at the level of the needle's distal end, which can then be extracted while keeping the biopsy away from the tapered end of the needle.

This method has the following disadvantages:
a) Often the biopsy is not kept away from the needle, either because it is not completely detached from the remaining tissue or because even a very slight depression is created inside the needle during tissue extraction and the biopsy aspiration that follows it, and the piece opposite from the tapered end of the needle cannot prevent this. This makes it necessary to repeat the entire process.
b) Other times the situation described above results in the biopsy partially coming out from the distal end of the needle, leading to traumatization and breakage of the biopsy cylinder as it moves back through the tissue as well as loss of a part of the distal portion of the biopsy.
c) The oscillation or oscillations performed on the needle in order to detach the biopsy always cause minimal breakage on the surface and in the hard tissue in which the needle is fixed. The width of this breakage slowly grows as the biopsy is pulled away from the surface of the tissue, with obvious suffering on the part of the patient and with changes in the needle's structure as it tends to bend and lose the necessary linearity.

SUMMARY OF INVENTION

The present invention is a device used with common hypodermic needles for the execution of a biopsy. This device has a structure which is introduced through the proximal end of the needle. The structure is guided by a handle and is inserted by pressure between the internal structure of the needle and the cylindrically-shaped hard tissue removed for biopsy. The device is made of a thin plate having a curvature to fit between the internal surface of the needle and the external surface of the biopsy cylinder.

DETAILED DESCRIPTION OF THE INVENTION

This invention is a complementary apparatus for common commercial needles used for percutaneous biopsy of hard tissue, particularly osteomedullary tissue.

Figure 1:
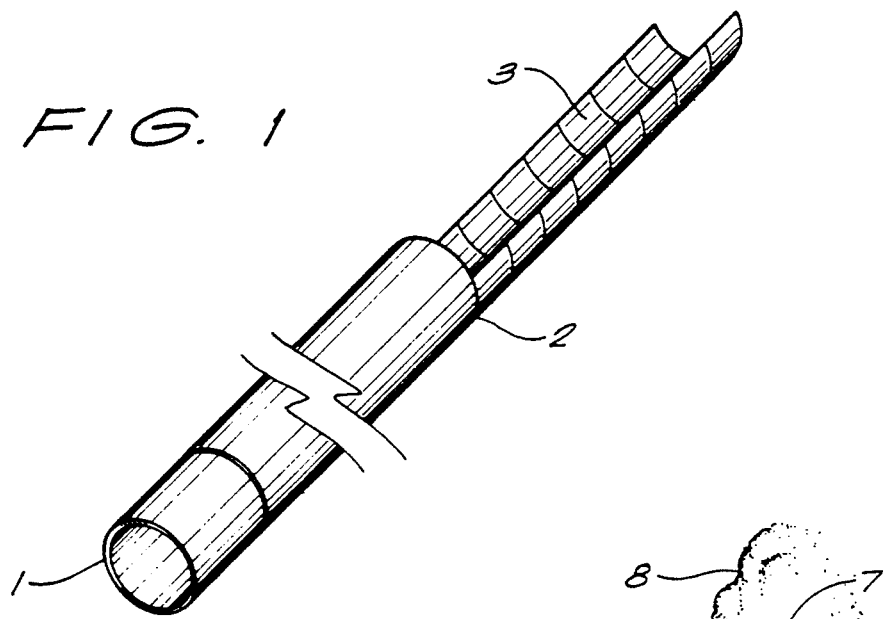
FIG. 1 is a perspective view of the apparatus prior to the removal of biopsy material.
Figure 2:
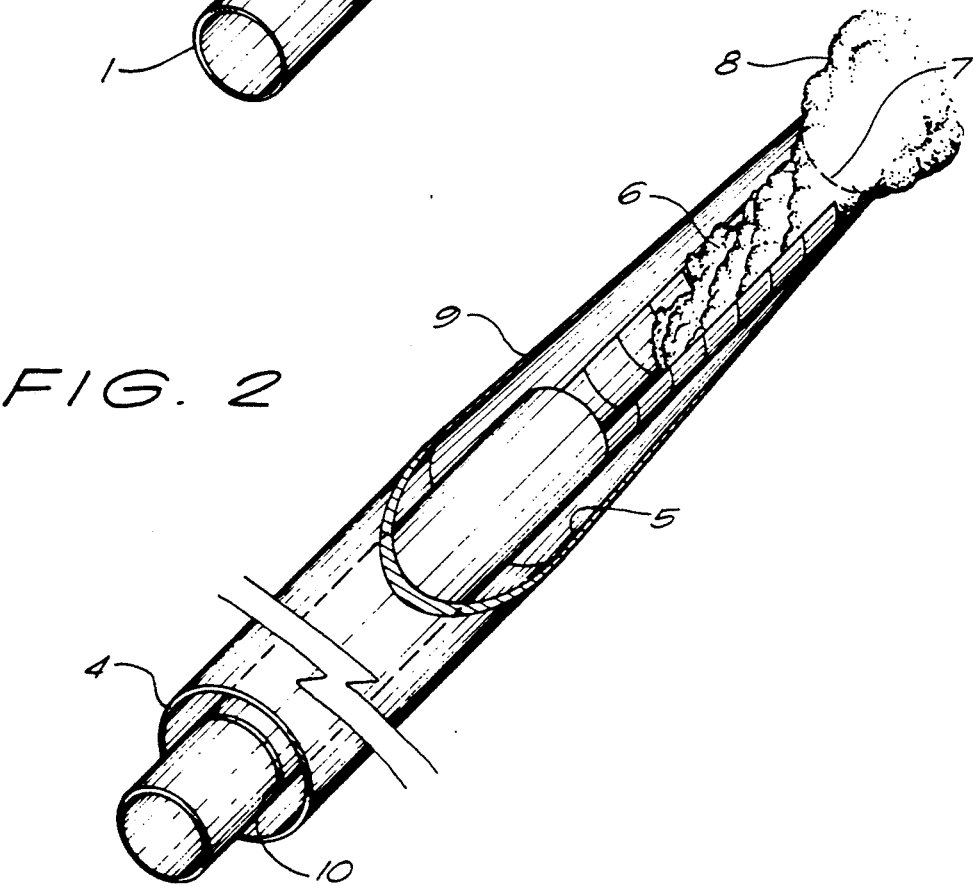
FIG. 2 is a perspective view of the apparatus of the present invention as used in a needle during the removal of biopsy material.

A simplified, non-limiting form of this apparatus is represented in the schematic drawings attached hereto as FIGS. 1 and 2. As handle-guide 1 continues to its distal end 2 in a thin plate 3, it curves to the lesser dimension according to a ray of curvature which allows introduction of it into the edge of the needle from its proximal end 4, following the internal surface of the needle 5. The plate is wide enough to cover about a third of the needle's transversal section and is longer than the longest biopsy which can be taken with that needle. The plate is introduced into the needle when the needle has already been inserted into the tissue and already contains the biopsy 6, and its distal end 7 is still continuous with the rest of the tissue 8. The thinness of the plate must be less than the space between the biopsy cylinder and the internal surface of the needle above its distal tapered end 9 but not less than the limit which guarantees rigidity during the maneuver described below. This very, thinness makes it possible for the plate to run along the needle's internal surface and insert itself between that and the tissue biopsy cylinder. When the plate is pushed forward in the needle so that it reaches the beginning of the tapered portion it is then pushed centrally towards the central axis of the needle in order to reduce the ray of curvature of the needle and it therefore touches the biopsy cylinder and meets with the cylinder's curved surface and begins to exert pressure on it. This pressure is exerted, advancing the plate further until blockage of the biopsy cylinder inside the needle against the opposite surface of the plate is guaranteed, without however altering the architecture of the biopsy tissue: rather to this it provides adequate calibration of the length of the apparatus introduced into the needle, through a reference 10 brought to the proximal end of the handle guide, in order to make it even with the proximal end of the needle 4. At this point the needle is rotated repeatedly in the same direction on its major axis, without leaving any signs of advance or retraction, nor the signs of oscillation necessary when using the traditional method mentioned in the premise. The rotation of the biopsy dragged into the needle, which is made solid by the plate, causes the complete interruption of any connection between the distal end of the biopsy 7 and the rest of the tissue 8. At this point, after having extracted the needle from the biopsied tissue, the plate will be extracted from the proximal end of the needle, and the plate will bring the biopsy cylinder with it in its concave space.

I claim:

1. A method for obtaining a biopsy of rigid tissue comprising the steps of:
    inserting a needle into the rigid tissue such that said needle contains a biopsy in a distal end, said needle being tapered at said distal end;

inserting a plate into a proximal end of said needle, said plate having a thinness suitable for fitting between an internal surface of said needle and an external surface of said biopsy;

passing said plate along an internal surface of a tapered portion of said needle until the plate pushes the biopsy against an opposite internal surface of said needle; and rotating said needle until said biopsy is separated from said rigid tissue.

2. The method of claim 1, further comprising the step of:

forming said plate so as to have a curvature less than a radius of said needle and a circumference of less than 360°.

3. The method of claim 2, said step of forming further comprising:

forming said plate such that said plate has a width equal to approximately a third of a transverse section of said needle, said plate having a length greater than said biopsy.

4. The method of claim 2, said step of forming further comprising:

affixing said plate to a handle, said handle extending outwardly of a proximal end of said needle when said plate is pushed through said needle.

5. The method of claim 4, said step of forming further comprising:

marking a reference point on a surface of said handle, said reference point being indicative of a limit of travel of said plate within said needle.

6. The method of claim 5, said step of passing comprising:

passing said plate into said needle until said reference point aligns with said proximal end of said needle.

7. The method of claim 1, said step of passing comprising:

pushing said plate until said plate causes said rigid tissue to be flush against said opposite internal surface of said needle.

8. The method of claim 1, said step of rotating comprising:

rotating said needle through a plurality of rotations in the same direction about an axis of said needle.

9. The method of claim 8, said step of rotating further comprising:

separating said biopsy from said rigid tissue at said distal end of said needle.

10. The method of claim 1, further comprising the steps of:

extracting said needle and said plate from said rigid tissue; and removing said biopsy from said needle.

11. The method of claim 10, said step of removing comprising:

pulling said plate from said needle through said proximal end of said needle, said biopsy remaining within a concave surface of said plate.

* * * * *